United States Patent
Wheelock

(10) Patent No.: US 8,218,878 B2
(45) Date of Patent: Jul. 10, 2012

(54) CUMULATIVE TIME-RESOLVED EMISSION TWO-DIMENSIONAL GEL ELECTROPHORESIS

(75) Inventor: Åsa Wheelock, Stockholm (SE)

(73) Assignee: HiKari Bio AB, Stockholm (SE)

( * ) Notice: Subject to any disclaimer, the term of this patent is extended or adjusted under 35 U.S.C. 154(b) by 461 days.

(21) Appl. No.: 12/454,334

(22) Filed: May 15, 2009

(65) Prior Publication Data

US 2009/0316992 A1 Dec. 24, 2009

Related U.S. Application Data

(60) Provisional application No. 61/054,300, filed on May 19, 2008.

(51) Int. Cl.
G06K 9/46 (2006.01)
G01N 27/447 (2006.01)

(52) U.S. Cl. .................................. 382/190; 382/128

(58) Field of Classification Search .................. 382/128, 382/190
See application file for complete search history.

(56) References Cited

U.S. PATENT DOCUMENTS 7,049,074 B2 * 5/2006 Schwartz ..................... 435/6.16

OTHER PUBLICATIONS

Pelet, S. et al., 2004. A Fast Global Fitting Algorithm for Fluorescence Lifetime Imaging Microscopy Based on Image Segmentation, Biophys. J. 87:2807-2817.
Alban, A et al., 2003. A novel experimental design for comparative two-dimensional gel analysis: two-dimensional difference . . . Proteomics 3:36-44.
Bartolome, A. et al., 2005. Fatty acid sensor for low-cost lifetime-assisted ratiometric sensing using a fluorescent fatty acid binding protein. Anal. Biochem. 345:133-139.
Clapp, AR et al., 2005. Can luminescent quantum dots be efficient energy acceptors with organic dye donors? J. Am. Chem. Soc. 127:1242-1250.
Handl, HL et al., 2005. Lanthanide-based luminescent assays for ligand-receptor interactons. Life Sci. 77:361-371.
Lassiter, SJ et al., 2000. Time-resolved fluorescence imaging of slab gels for lifetime base-calling in DNA sequencing applications. Anal. Chem. 72:5373-5382.
Spiess, PC et al., 2008. Measurement of protein sulfhydryls in response to cellular oxidative stress using gel electrophoresis and mul . . . Chem. Res. Toxicol. 21:1074-1085.
Stryjewski, W et al., 2002. Multiplexed analysis using time-resolved near-IR fluorescence for the detection of genomics material. Proc. SPIE 4626:201-209.
Wheelock, AM et al., 2005. In vivo effects of ozone exposure on protein adduct formation by 1-nitronaphthalene in rat lung. Am. J. Respir. Cell Mol. Biol. 33:130-137.
Wheelock, AM et al., 2006. Use of a fluorescent internal protein standard to achieve quantitative two-dimensional gel electrophoresis. Proteomics 6:1385-1398.

* cited by examiner

Primary Examiner — Joseph Chang
(74) Attorney, Agent, or Firm — Lynn E. Barber

(57) ABSTRACT

A new instrumental design is provided for in-gel detection and quantification of proteins. This new platform, called Cumulative Time-resolved Emission 2-Dimensional Gel Electrophoresis, utilizes differences in fluorescent lifetime imaging to differentiate between fluorescence from specific protein labels and non-specific background fluorescence, resulting in a drastic improvement in both sensitivity and dynamic range compared to existing technology. The platform is primarily for image acquisition of two-dimensional gel electrophoresis, but is also applicable to protein detection in one-dimensional gel systems as well as proteins electroblotted to e.g. PVDF membranes. Given the increase in sensitivity of detection and dynamic range of up to 5-6 orders of magnitude compared to existing approaches, the described invention represents a technological leap in the detection of low abundance cellular proteins, which is desperately needed in the field of biomarker discovery.

14 Claims, 12 Drawing Sheets

CUMULATIVE TIME-RESOLVED EMISSION TWO-DIMENSIONAL GEL ELECTROPHORESIS

CROSS-REFERENCE TO RELATED APPLICATIONS

This application claims priority from U.S. provisional application Ser. No. 61/054,300 filed May 19, 2008.

BACKGROUND OF THE INVENTION

1. Field of the Invention

The present invention relates to a method and new image acquisition technology for in-gel detection and quantification of proteins. This new platform, called Cumulative Time-resolved Emission 2-Dimensional Gel Electrophoresis (CUT-EDGE™), utilizes differences in fluorescent lifetimes to differentiate between fluorescence from specific protein labels and non-specific background fluorescence, resulting in a drastic improvement in both sensitivity and dynamic range compared to existing technology.

2. Background of the Invention

"Proteomics" refers to the study of the protein complement of the genome (proteome), a term coined by Marc Wilkins in 1994. Over the past decade, many methodologies for simultaneous quantification of thousands of proteins in a cell or tissue have been developed and utilized for e.g. biomarker discovery or mechanistic studies of cellular processes. Two-dimensional gel electrophoresis (2-DGE) was the first method to be adapted for global proteomics analysis, and still constitutes one of the workhorses in proteomics research. The 2-DGE method involves separation of complex protein samples according to charge in the first dimension and according to size in the second dimension, resulting in a 2-D map of protein spots where ideally each spot corresponds to a single protein species. The protein spots are then visualized with protein stains that bind stoichiometrically to the proteins, thus providing a third dimension that corresponds to protein abundance, which facilitates quantitative proteome analysis.

Problems with large gel-to-gel variations associated with the original 2-DGE technique have been addressed through the incorporation of an internal standard, such as the Differential Gel Electrophoresis (DIGE) and Alexa-Labelled Internal Standard (ALIS) techniques. Both concepts are based on sample proteins and internal standard proteins being labeled with spectrally separated fluorochromes, and co-separated on the same 2-DGE gel. By ratiometric normalization the inter-gel variations can be corrected for, thus greatly improving the quantitative aspects and overall statistical power of the 2-DGE technique.

The major constraint remaining in current 2-DGE methodology is limitations in the sensitivity of detection. The fact that protein abundances in biological samples may span over as much as twelve orders of magnitude puts high demands both on sensitivity and dynamic range of protein stains used in quantitative 2-DGE. Towards this end, fluorescent stains with dynamic ranges of 3-4 orders of magnitude have replaced the use of classical calorimetric staining methods, such as silver and commassie stains with dynamic ranges typically limited to 1-2 orders of magnitude (FIG. 1).

Fluorescent dyes are available both for covalent labeling prior to 2-DGE separation (e.g. CyDyes™, Alexa-dyes), as well as for non-covalent, post-electrophoretic staining procedures (e.g. SYPRO Ruby™, Deep Purple™). However, even the best performing fluorescent probes for protein visualization currently on the market only cover a very small portion of the potential physiological range since physiological protein abundances range from a few molecules up to micromolar concentrations, while detection limits for the state-of-the-art method of minimal DIGE typically are limited to nanograms of protein (FIG. 1).

In current usage of fluorescence for protein detection and quantification in 2-DGE, the excitation of the fluor and the measurement of the resulting emission occur simultaneously. Being time efficient and practical from a technical standpoint, this approach is utilized in both fluorescent scanners and CCD-camera based 2-DGE image acquisition instruments. However, direct fluorescent measurements do not utilize the full potential of these fluorochromes. Biological specimens contain numerous auto-fluorescent components, and the polyacrylamide matrix itself emits background fluorescence to some extent. To optimize the signal-to-noise ratio, it is thus essential to decrease disturbances from background- and autofluorescence.

In current 2-DGE technology, attempts to remove the resulting background are made mathematically through software algorithms used in the post-electrophoretic computer-assisted quantitative analysis. However, we have previously shown that the majority of these background subtraction and correction algorithms alter the data and introduce additional variance into the quantification of protein spot volumes, as well as contribute to a skewed, non-normal distribution (1-4).

Through time-resolved fluorescence (TRF), the origin of a photon can be derived through separation of the decay curves of the various fluorescent species present in a given pixel. TRF is currently used in a number of applications in related fields, primarily microscopy applications to visualize localization, folding dynamics, or movement of proteins in solution (5, 6). Several of the fluorochromes currently used in 2-DGE have been utilized in time-resolved fluorescence applications in these related fields (e.g. CyDyes™ available from GE Healthcare, Uppsala, Sweden, and Alexa-dyes as well as ruthenium chelates such as SYPRO Ruby™, both available from Molecular Probes, Eugene, Oreg., USA (7, 8)). However, the lack of this feature in modern 2-DGE image acquisition equipment is currently prohibiting the use and development of TRF in 2-DGE.

3. Description of the Related Art

Most of the prior art in the field concerns fluorescence resonance energy transfer (FRET) techniques for the study of inter-molecule interactions, molecular stability, or intra-molecular conformational changes, and some concern the use of fluorescent lifetime imaging (FLIM). These include monitoring of polymerized chain reaction (PCR) products (Rintamaki S. et al, Journal of microbiological methods, (2002 August) Vol. 50, No. 3, pp. 313-8) and others for base calling in DNA sequencing (Lassiter S J et al, Analytical chemistry, 2000 Nov. 1, Vol. 72, No. 21, pp. 5373-82). These authors have modified the microscope head in an automated DNA sequencer to allow near-infrared time resolved fluorescent lifetime measurements. Accordingly, the design, capabilities, and utilization of this instrument were of an entirely different character than the invention herein. The instrument modifications performed by this group were designed for classification purposes in order to improve the accuracy and speed of DNA sequencing. In essence, lifetime imaging was utilized to distinguish between two fluorochromes with different lifetimes, representing the presence of different DNA fragments that were fractionated through slab gel electrophoresis. In follow-up studies, the authors expanded the sequencing technology to a polymer microchip platform with a similar purpose (Llopis S D et al, Electrophoresis, 2004 November, Vol.

25, No. 21-22, pp. 3810-9) as well as for reading fluorescent signatures from DNA microarrays (Stryjewski et al Proceedings of SPIE-The International Society for Optical Engineering (2002), 4626 (Biomedical Nanotechnology Architectures and Applications), 201-209). The use of multidimensional time resolved fluorescence for the background subtraction of the invention herein was never used in any of these applications. In contrast, the authors either went to great lengths to investigate which polymer support matrix gave rise to the least amount of background fluorescence in order to maintain a mono-exponential work flow, or alternatively used conventional background correction methods such as time gating or subtraction of the intensity of negative control spots. As such, the use of multi-exponential time resolved fluorescence for specific background subtraction in in-gel (protein) measurements of this invention represents a surprising effect and a novel technology.

An objective of the invention is to provide a new platform for in-gel detection and quantification of fluorescently labeled proteins in global proteome studies. The invention involves the utilization of fluorescent lifetime imaging (FLIM). Other objects and advantages will be more fully apparent from the following disclosure and appended claims.

SUMMARY OF THE INVENTION

A central embodiment of the CUTEDGE™ technology involves excitation of a fluorochrome bound to a protein (covalently or by ionic forces) with a pulsed laser scanner. The state-of-the-art fluorescent laser scanners currently used for image acquisition in quantitative 2-DGE utilize a constant light source for excitation. Constant illumination of the gel does not utilize the differences in fluorescent life time, and the detected emission corresponds to the joint peak emission of fluorochrome and background fluorescence. In contrast, scanning with a pulsed laser, using the invention described herein, provides FLIM measurements on a pixel-by-pixel level (FIGS. 2A-2C). The laser, presumably a diode laser, can be internally housed within a sealed scanner enclosure, or externally attached through fiberoptic cable outlets to provide optimal flexibility in terms of the excitation wavelengths, i.e. the specific diode lasers, to be used. As such, the technology may be provided as an up-grade for existing instrumentation, or as a fully enclosed scanner system.

An additional embodiment of the invention includes the utilization of multi-exponential fitting of the fluorescence decay curve to separate fluorescence originating from the fluorochrome-labeled protein species from fluorescence originating from other sources such as the gel matrix itself, solutions or particles presents in the gel, or scattering effects. The separation of the fluorescent decay curves provides background subtraction on the photon level as illustrated in FIGS. 2A-2C. In addition, this embodiment of the CUTEDGE™ technology reduces the need for software-assisted background subtraction algorithms in the subsequent image analysis, and the increased experimental variance known to be introduced by these algorithms. The distribution of the fluorescent lifetimes in a 2-DGE image is exemplified by FIGS. 4A-4B, which illustrates a pseudocolored lifetime image of a Cy2.

Yet another embodiment of the invention herein involves sequential use of multiple laser wavelengths for excitation to facilitate a combination of TRF with spectral separation of fluorochromes. Spectral separation is used in current 2-DGE protocols to facilitate correction of inter-gel variations in separation patterns through multiplexing, such as the DIGE (9) and ALIS (10) approaches. Multiplexing protocols for incorporation of an internal standard in 2-DGE are vital for correction of gel-to-gel variations inherent in the 2-DGE method, and are well established in the field of gel-based proteomics. As such, inclusion of this embodiment makes the CUTEDGE™ instrument easy to implement in existing proteomics work flows using current protocols for internal standard in 2-DGE. The use of multiplexing through spectral separation rather than through TRF also decreases the complexity of the life time decay spectra, thus improving the background subtraction capability of the CUTEDGE™ method. However, dual FLIM measurements may also be included in cases where the excitation wavelength and fluorescent lifetimes of the incorporated fluorochromes are compatible, as is the case for the Cy2/Cy3 dye pair (Example 4).

The incorporation of a photon detector of sufficient sensitivity as well as dynamic range represents yet another crucial embodiment of the invention. Traditionally, Photomultiplier Tube (PMT) technology has been used in image acquisition instruments for 2-DGE to assure a broad dynamic detection range. However, the limited quantum efficiencies (QE) of PMT detectors may compromise the sensitivity of detection in the CUTEDGE™ application. As such, Avalanche Photo Diode (APD) detectors, with QEs up to 90% in the visible range, may prove to be advantageous in terms of sensitivity, with the down side of potential limitations in the dynamic range of detection. As such, different variants of the CUTEDGE™ instrument equipped with detectors matching the user's individual needs may be designed as known in the art.

Integration of the intensity fluorescent decay curve specific for the fluorochrome to calculate the area under the curve (AUC) represents yet another central embodiment of the invention. Utilizing the AUC (corresponding to the total photon count for the fluorochrome component) as the output format rather than the amplitude contribution of the component is estimated to provide an additional 1-2 orders of magnitude improvement in dynamic range.

Automation and user-friendliness are a core component of the CUTEDGE™ instrument, particularly in terms of graphical and quantitative calculations of acquired 2-DGE image. Automated protocols for FLIM analysis, subtraction of the background components, and export of intensity images for the fluorochrome component(s) are included for the standard fluorochromes used in 2-DGE. In order to facilitate the use of existing 2-DGE image analysis software, the AUC is thus represented as a one-dimensional (Z) intensity in the resulting exported image. The use of a 32 bit Tagged Image File Format (TIFF) or equivalent in replacement of the currently used 16 bit format provides a digital dynamic range of close to 10 orders of magnitude, thus facilitating the full dynamic range of pixel intensities achieved through the CUTEDGE™ technology.

To maximize automation, the invention also facilitates programming of sequential scanning of multiple different protocols as defined by the user, for example sequential scanning of multiple fluorochromes used for multiplexing.

Given the wide range of fluorescent lifetimes available in the various fluorescent probes used in gel-based proteomics today, variable frequency pulsed laser diodes for optimization of scan times represent another embodiment of the invention.

There has thus been outlined, rather broadly, the more important features of the invention in order that the detailed description thereof may be better understood, and in order that the present contribution to the art may be better appreciated. There are additional features of the invention that will be described hereinafter.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

DETAILED DESCRIPTION OF THE INVENTION

Figure 1:
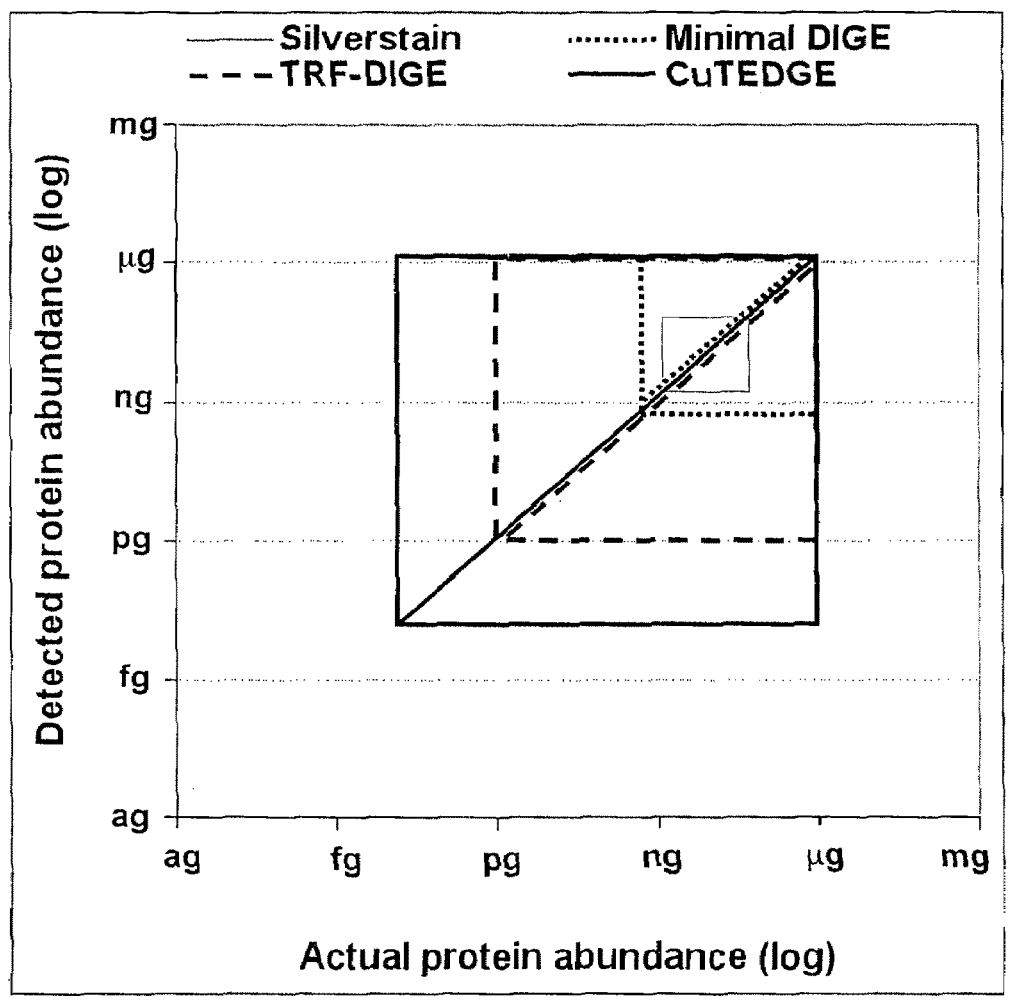
FIG. 1 shows detected protein abundance vs. actual protein abundance with silver stains (thin solid line) and state-of-the-art fluorescent DIGE measurements (dotted lines) as well as comparison of initial proof-of-principle measurements using DIGE fluorochromes with sub-optimal TRF instrumentation (dashed lines) with measurements using the invention herein (thick solid lines).

The invention herein provides a new platform for in-gel detection and quantification of fluorescently labeled proteins in global proteome studies and basically has the following embodiments as discussed in more detail herein: The general design of the CUTEDGE™ instrument is outlined in FIG. 6. A pulsed laser diode, internally housed within a sealed scanner enclosure or externally attached through a fiberoptic cable, is used for in-gel excitation of fluorochrome-labeled proteins (covalently or by ionic forces). A scanner mechanism, provided through movement of the glass platen holding the gel or alternatively, but moving dichroic mirrors underneath the gel platen, facilitates pixel-wise scanning of the gel. The emitted fluorescence passing through the moving/stationary dichroic filter will be directed through an emission filter of choice and further through a fiberoptic cable to an internally housed or externally attached detector, depending on whether the instrumental design concerns an enclosed scanner system or an external up-grade kit. The photon counting board exports transfers the data to a software module, which is designed for fully automated multi-exponential lifetime fitting of the fluorescence decay curve to separate fluorescence originating from the fluorochrome-labeled protein species from fluorescence originating from other undesirable background fluorescence. The integrated fluorescent decay curve specific for the fluorochrome is exported as one intensity image per fluorochrome, in a format compatible with further quantitative 2-DGE image analysis.

The invention herein, by utilizing the intrinsic differences in fluorescent decay times of fluorochromes and background fluorescence, respectively, both overall signal intensity and signal-to-noise ratios can be significantly improved in gel-based proteomics. Through use of pulsed lasers, the decay curves throughout the fluorescent lifetime can be measured, as illustrated in FIGS. 3A-3D. A mechanism for moving the laser pulse and detector across the gel will be used to facilitate a pixel-wise scanning of the gel. One solution involves a stepper motor controller to move a set of mirrors underneath a stationary glass platform holding the gel to avoid movement of the actual gel platform. This inverted set-up helps keeping the slab gels stationary to avoid rapture of the fragile polyacrylamide gels, particularly in large format gels. The resulting variable distance caused by the moving mirrors will be corrected for by the appropriate placement of delay generators. In addition, this solution facilitates a robust enclosure to allow water immersion of the slab gels, which otherwise can dry out during the high resolution, sequential scanning required for multiplexing. An alternative solution involves stepwise movement of the scanner board holding the gel. Importantly, either set-up provides easy exchange of the pulsed diode laser to facilitate flexibility in the choice of excitation wavelengths.

The most straightforward utilization of TRF is to calculate the average lifetime from the detected photon emission curve. Less sophisticated TRF measurements where multi-exponential fitting is omitted are primarily utilized to determine the absence or presence of a known fluorochrome. In complex systems such as the in-gel detection of Cy2-labelled proteins exemplified in FIG. 2A, the contribution of the background components cannot be distinguished from the emission derived from the fluorochrome. Non-TRF measurements using a constant light source results in a constant emission level corresponding to the peak level of the total fluorescence (solid line), and in resemblance to mono-exponential TRF measurements, the individual background components cannot be distinguished from the total fluorescence.

Figure 2A:
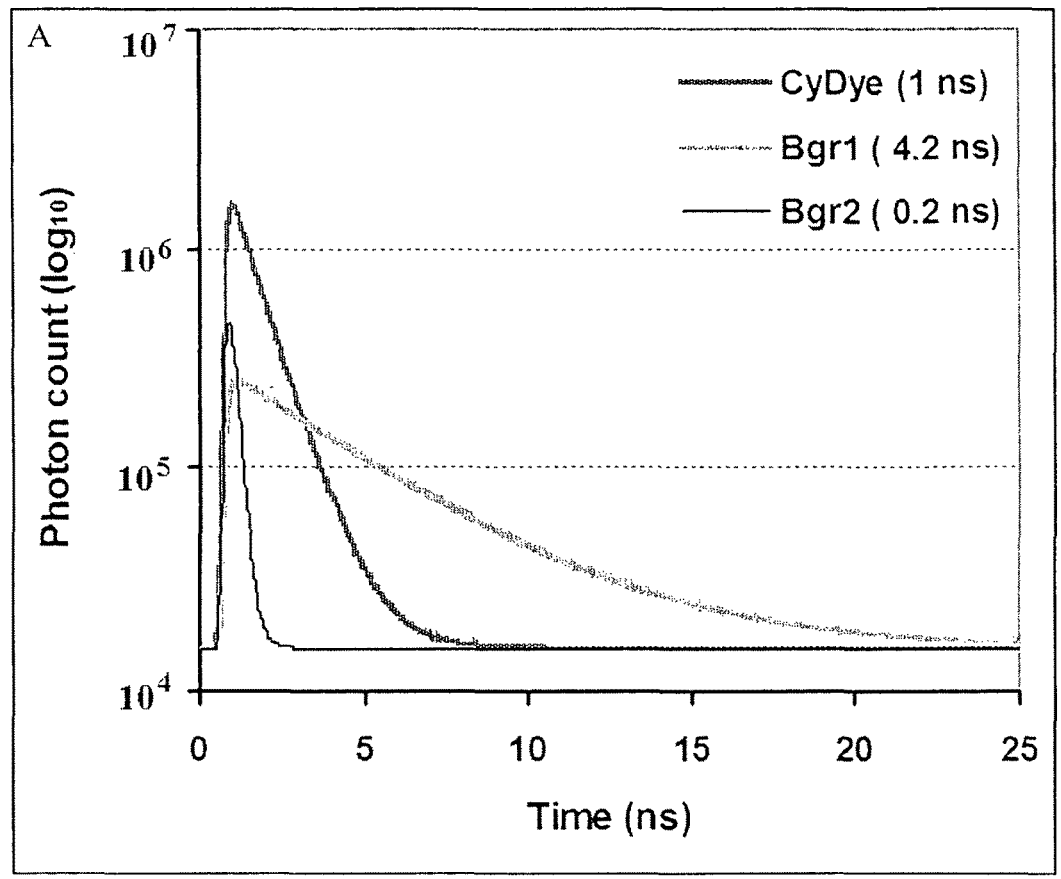
FIG. 2A shows an example of multi-exponetial fitting of the fluorescence decay curves (photon count vs. time) resulting from in-gel measurements of CyDye-labelled proteins.
Figure 2B:
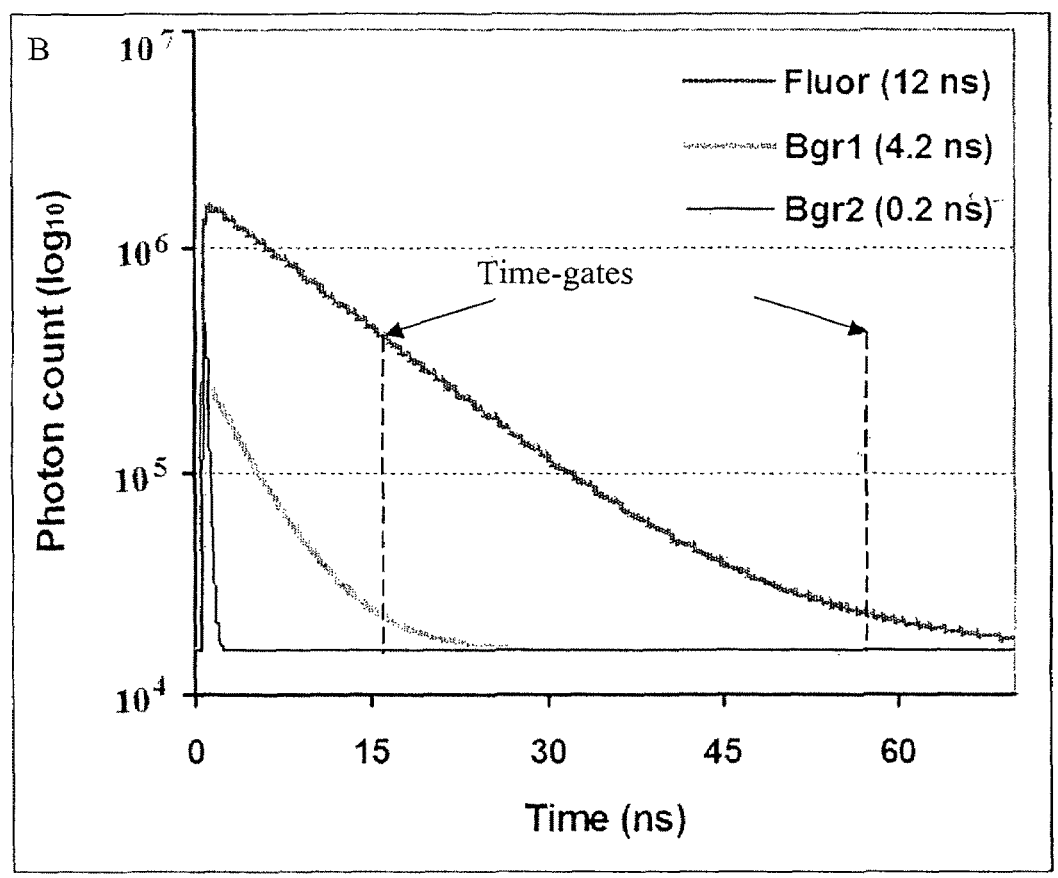
FIG. 2B shows an example of multi-exponetial fitting of the fluorescence decay curves (photon count vs. time) using flourochromes with a longer fluorescent lifetime, with the optimal window for time-gated measurements indicated (dashed lines).
Figure 2C:
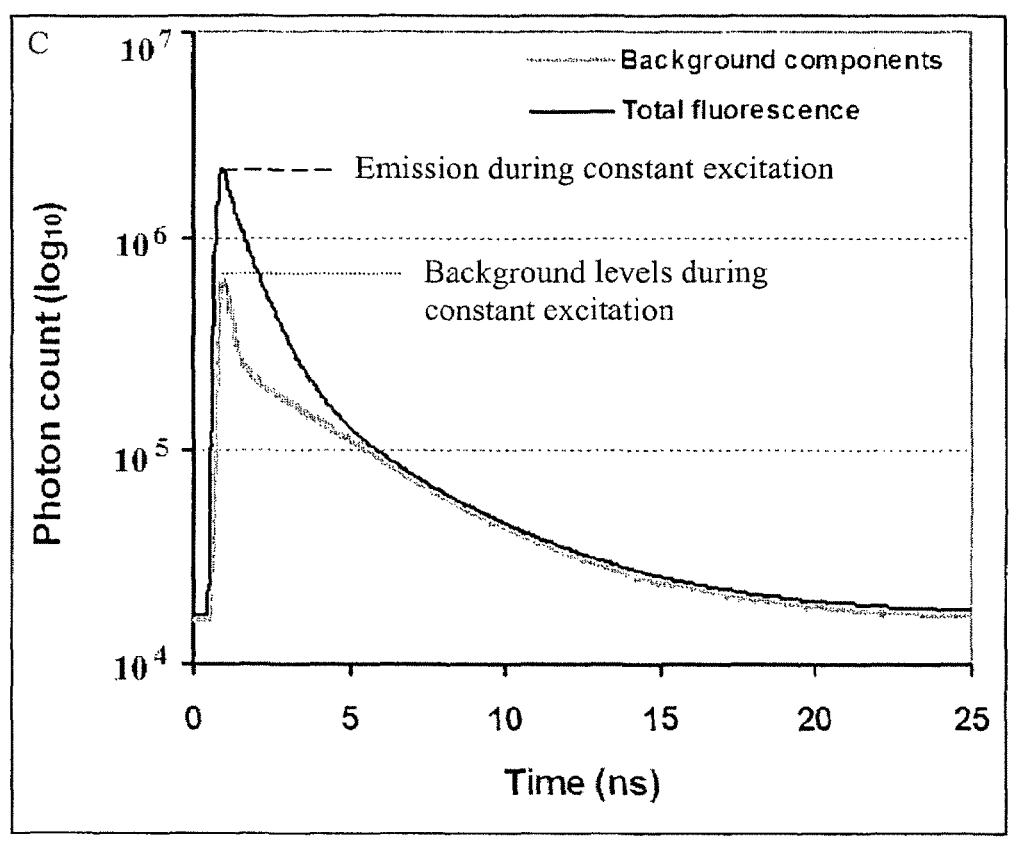
FIG. 2C is a graph comparing the cumulative background fluorescence contribution with the total fluorescence. Emission levels during standard, non-time resolved measurements are indicated (dashed line)

The resulting mono-exponential fitting does not facilitate separation of multiple fluorescent components, and as a result the emission from background and fluorophor are summarized in one single curve (FIG. 2C; solid line). As such, the resulting mono-exponential FLIM measurements are better suited for discrimination between the presence/absence of fluorochromes of known lifetimes, as exemplified by the mono-exponential TRF instrument mentioned in "Description of the Related Art" constructed for binary classification of nucleotides in Sanger DNA sequencing and detection of nucleotides in microarrays (11, 12). The application to 2-DGE gel images intended by the CUTEDGE™ technology represents numerous challenges as compared to previous TRF applications for DNA microarrays. Most importantly, the spot locations and spot sizes in microarrays are known, making it easy to pre-define the spot boundaries. In contrast, neither the spot size nor the spot locations are known in 2-DGE since the spot pattern is based on the physiochemical properties of the proteins. Large inter-gel variations in spot separation patterns further add to the complexity of spot detection and quantification in 2-DGE images. The solid surfaces used in microarrays are much more homogenous than the polyacrylamide gel matrix used in 2-DGE. The in-gel localization of the proteins in 2DE results in a more complex background fluorescence than the on-top hybridization utilized for detection of nucleotides in microarrays. As such, a much more robust system in terms of background detection and subtraction is required for 2-DGE image acquisition as compared to microarray imaging systems.

Since the background fluorescence cannot be quantified in conventional fluorescence applications, the background emission has to be estimated through evaluation of the intensity of the pixels surrounding the fluorescently labelled molecule. Currently available algorithms for background subtraction in 2-DGE images are not very accurate, and we have previously shown in a number of publications that these algorithms lack in robustness in terms of reproducibility, and as such introduce a significant amount of variance in the quantitative analysis (1-4).

Given that a sufficient separation in life time of the background fluorescence and fluorochrome exists, mono-exponential TRF applications can provide an improvement over constant illumination measurements in that the background noise can be reduced through time-delayed measurements (FIG. 2B). However, time-gating aimed to exclude the background emission generally results in exclusion also of the main emission peak of the fluorophor (FIG. 2B). In cases where the lifetime of the fluorochrome is substantially longer than the background components, time-gated measurements can be used to exclude the background fluorescence from the quantification. While this strategy will compromise the improvements in signal-to-noise ratio somewhat, the need for complex fitting algorithms can be excluded once the lifetimes of the existing components are known. Accordingly, the gain in sensitivity and dynamic range is limited, as evidenced by previous attempts to apply mono-exponential time-delayed approaches to microarrays (12).

In addition, the cyanine-based fluorophores most frequently used in 2-DGE today (DIGE CyDyes) have fluorescent lifetimes that are much shorter than that of the surrounding polyacrylamide matrix (~1 ns versus ~4 ns; FIG. 2A), thus excluding the time-gating strategy. As such, the use of deconvolution algorithms for multi-exponential decay are a central aspect of the CUTEDGE™ technology to facilitate FLIM-based background subtraction also for these short-lifetime fluorochromes.

Figure 5:
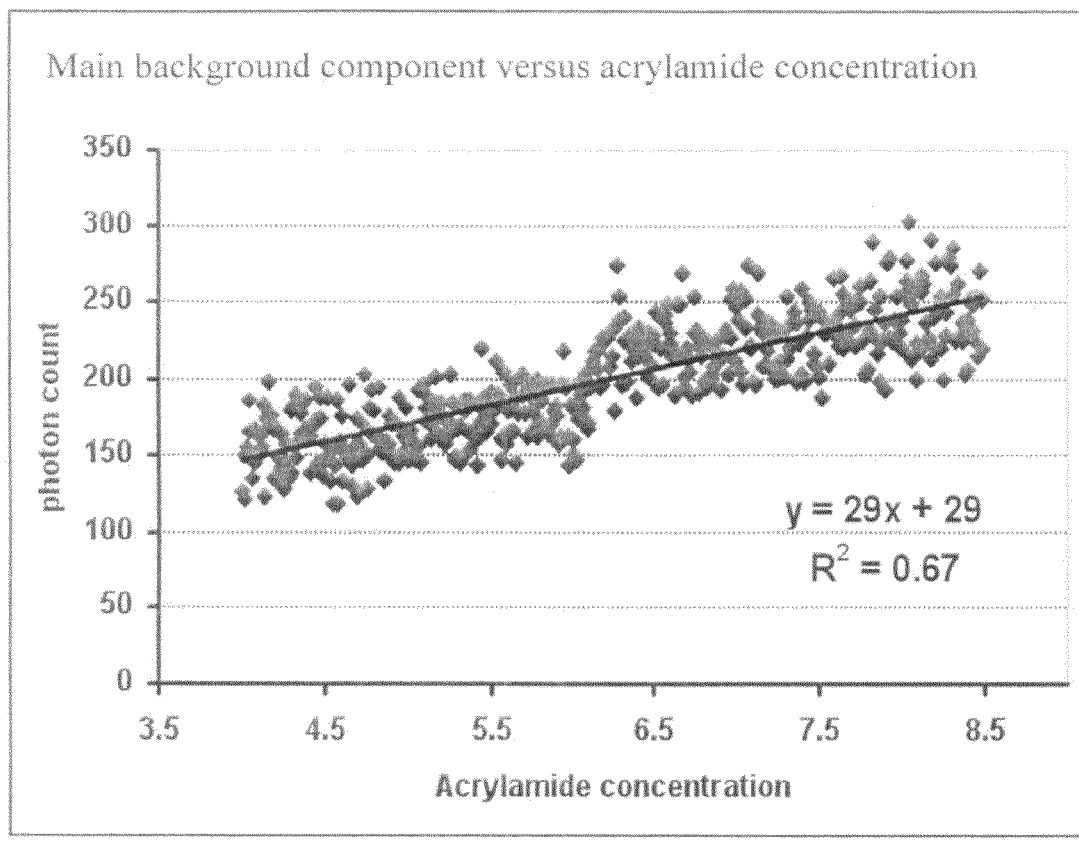
FIG. 5 is a graph of photon count vs. acrylamide concentrations for the long main background component (4.2 ns) in a 1-dimensional gradient gel.

In FIG. 2A showing in time-resolved fluorescence (TRF), a pulsed laser is utilized for excitation (time 0), and the subsequent fluorescence decay curve is quantified. Multi-exponential fitting of the decay curve resulting from detection of in-gel detection of Cy2-labelled proteins revealed a short background component (0.2 ns) and a long background component (4.2 ns) in addition to the fluorochrome component (1 ns). FIG. 5 shows the strong correlation between the intensity of the main background component (4.2 ns) and the acrylamide concentration in a gradient polyacrylamide gel ($R^2$=0.67), indicating that the polyacrylamide matrix is the source of this background component. The lifetime of the component remained stabile throughout the polyacrylamide gradient, and only the intensity of the component was altered. As such, the background subtraction strategy to be used in the CUTEDGE™ technology is a robust method applicable to gradient gels as well as isocratic gels of varying concentrations. Multi-exponential fitting facilitates subtraction of the background components, which result in a significantly increased signal-to-noise ratio.

Figure 4:
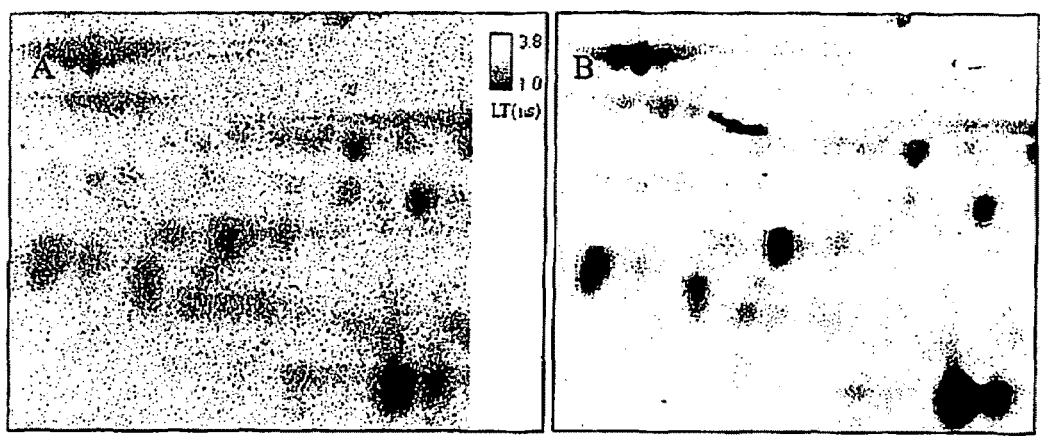
FIG. 4A shows a pseudocolored lifetime image displaying the distribution of the different lifetime components in a 2-DGE gel containing Cy2-labelled proteins. The temporal scale is displayed in the right upper corner, with white representing the longest and black the shorter lifetimes. The salt-and-pepper appearance in the non-spot regions of the image results from a very short background component (0.2 ns) mixed with the longer background component (4.2 ns) associated with the acrylamide matrix (see FIG. 5).
FIG. 4B shows the protein spot pattern of the corresponding conventional 2-DGE image displaying total fluorescent intensities (without lifetime separation) corresponds well with the lifetime image, indicating that the background components of the polyacrylamide gel indeed are distinctly separable from that of the CyDye fluorochromes through lifetime fluorescence applications.

Proof-of-principle experiments using the 3-plexed set of DIGE fluorochromes (Cy2, Cy3 and Cy5) showed a distinct difference in the distribution of lifetimes of the background components and the fluorochrome itself (FIGS. 4A). A comparison between the traditional intensity image and a pseudo-colored lifetime image clearly demonstrate that the protein spot separation pattern is superimposable. Pixel-wise multi-exponential fitting and subsequent extraction of fluorochrome component thus facilitates background subtraction on a photon level. Proof-of-principle measurements revealed a more than 10-fold increases in signal-to-noise ratios over existing top-of-the-line laser scanners, even though sub-optimal instrumentation was utilized (a modified TRF microscope allowing a maximal measurement depth of ~1 μm, as compared to a Typhoon scanner measuring the full 1 mm depth of the gel). As shown in FIG. 1, the range of physiological protein abundances (x-axis) plotted against the linear detection range for various protein stains used in 2-DGE (y-axis). Colorimetric methods such as silver stain (light solid line) typically offer a dynamic range of 1-2 orders of magnitude, while fluorescent methods such as minimal DIGE (dotted line) provide linear dynamic ranges of 3-4 orders of magnitude. Proof-of-principle measurements using existing (dashed line) TRF instrumentation showed a 3 order of magnitude improvement in dynamic range when applying TRF in standard DIGE measurements (thick solid line). Following implementation of the embodiments outlined for the novel CUTEDGE™ instrument, the dynamic range and sensitivity of detection are estimated to improve with an additional 2-3 orders of magnitude (solid-line box). As such, this central embodiment alone is expected to provide several orders of magnitude improvements in sensitivity and dynamic range over existing image acquisition techniques for 2-DGE. The resulting increase in specificity in the measurement provides not only a higher sensitivity, but also eliminates confounding factors from scattering effects or other fluorescent species present in the gel, including the gel matrix itself, solvents, particles or cellular debris remaining in the gel. In addition to improvements in the signal-to-noise ratio of the detection, the multi-exponential FLIM approach thus also contributes to reduce problems with segmentation (spot detection) and registration (spot matching) in the subsequent image analysis. Such problems currently represent another major bottleneck in the quantitative 2-DGE work flow, as extensive manual editing of the automated spot detection and matching is needed today. The cleaner background produced by the CUTEDGE™ technology will thus improve automation of the image alignment and ultimately reduce the subjectivity of the image analysis. Software-induced variance introduced by currently used background subtraction algorithms in 2DGE analysis software is also eliminated, as such algorithms no longer are necessary.

Multiplexing through the use of spectrally separated fluorochromes is a well established approach to compensate for the large gel-to-gel variations inherent in the 2-DGE separation technique. However, in most TRF applications, multiplexing is achieved through the use of fluorochromes with differing fluorescent lifetimes, while the excitation and emission spectra overlap. To maximize the versatility of the CUTEDGE™ methodology, we will combine the spectral and temporal separation into one application. As such, multiple laser wavelengths will be used for excitation as illustrated in Example 2. This facilitates a combination of TRF with the spectral separation currently used in e.g. the DIGE (9) and ALIS (10) approaches, thus making the CUTEDGE™ instrument easily implemented in existing proteomics work flows using current protocols for internal standard in 2-DGE. In multiplexing using existing image acquisition instrumentation, a longer acquisition time will not have any discernable effect on quantitation.

Figure 3A:
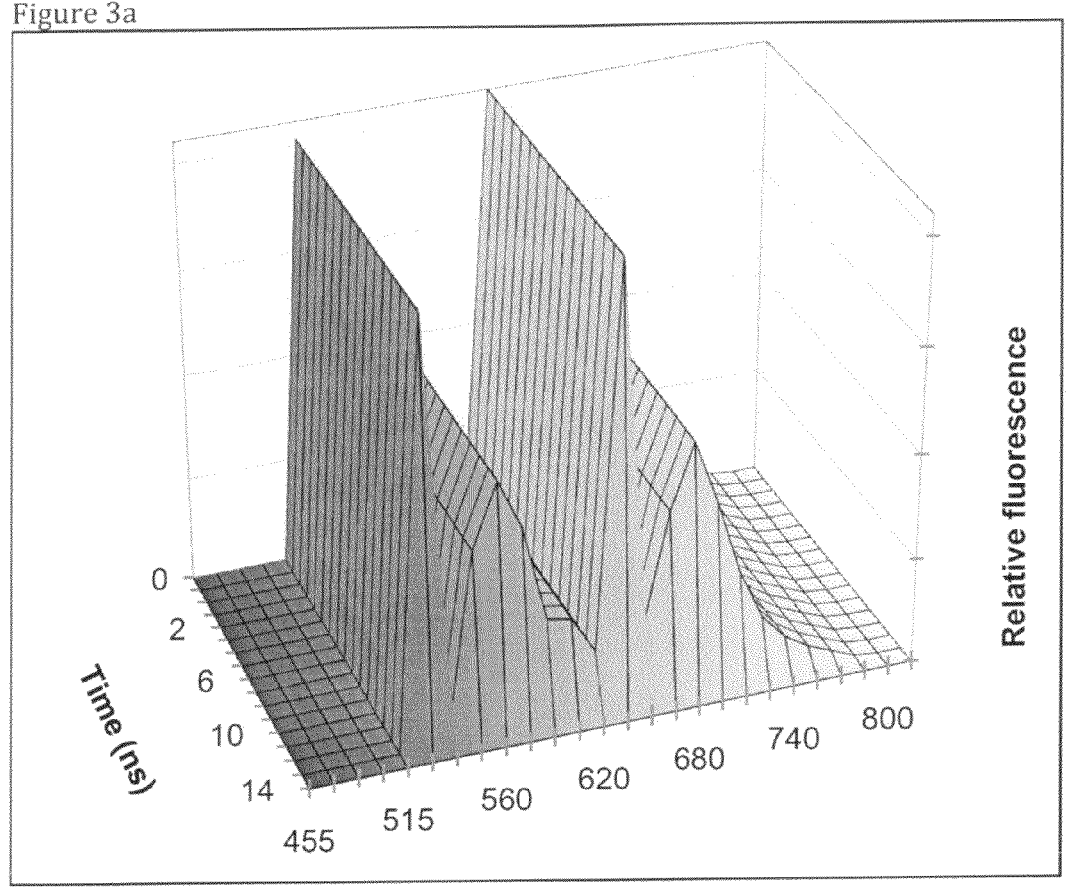
FIG. 3A shows a three-dimensional graph of relative fluorescence, wavelength and time for Cy3 and Cy5 during excitation with a constant light source.
Figure 3B:
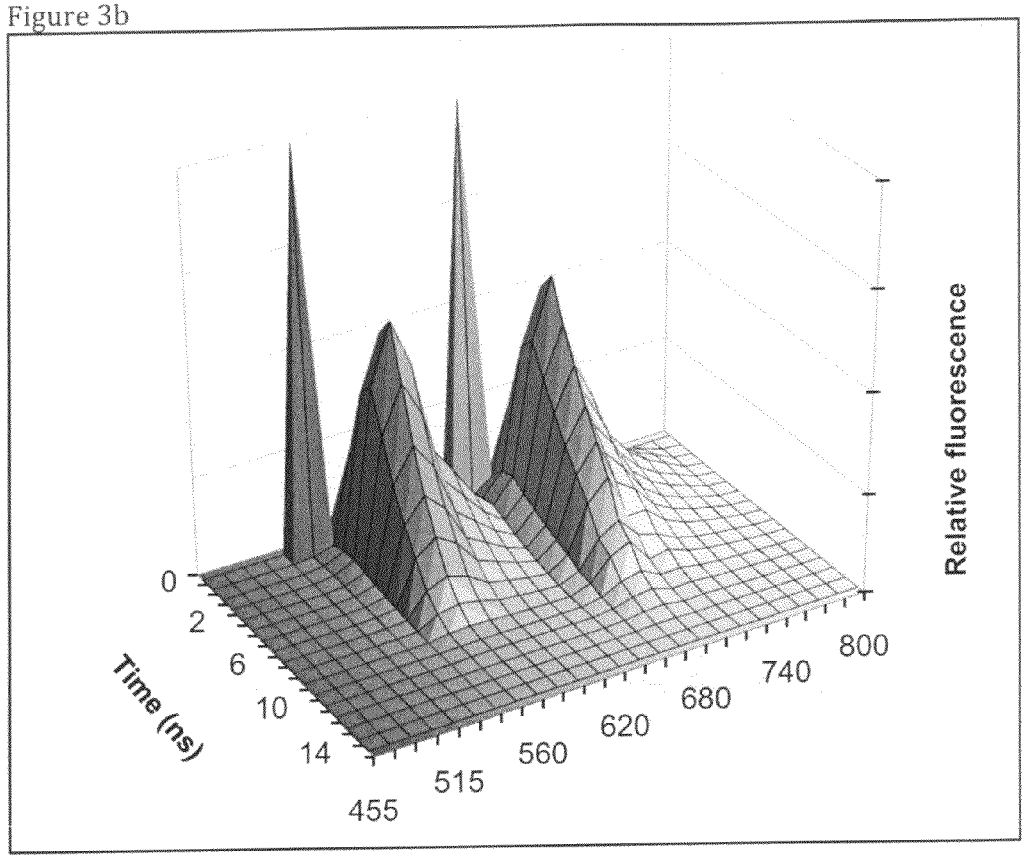
FIG. 3B shows a three-dimensional graph of relative fluorescence, wavelength and time for Cy3 and Cy5 during time resolved measurements, i.e. excitation with a pulsed laser.
Figure 3C:
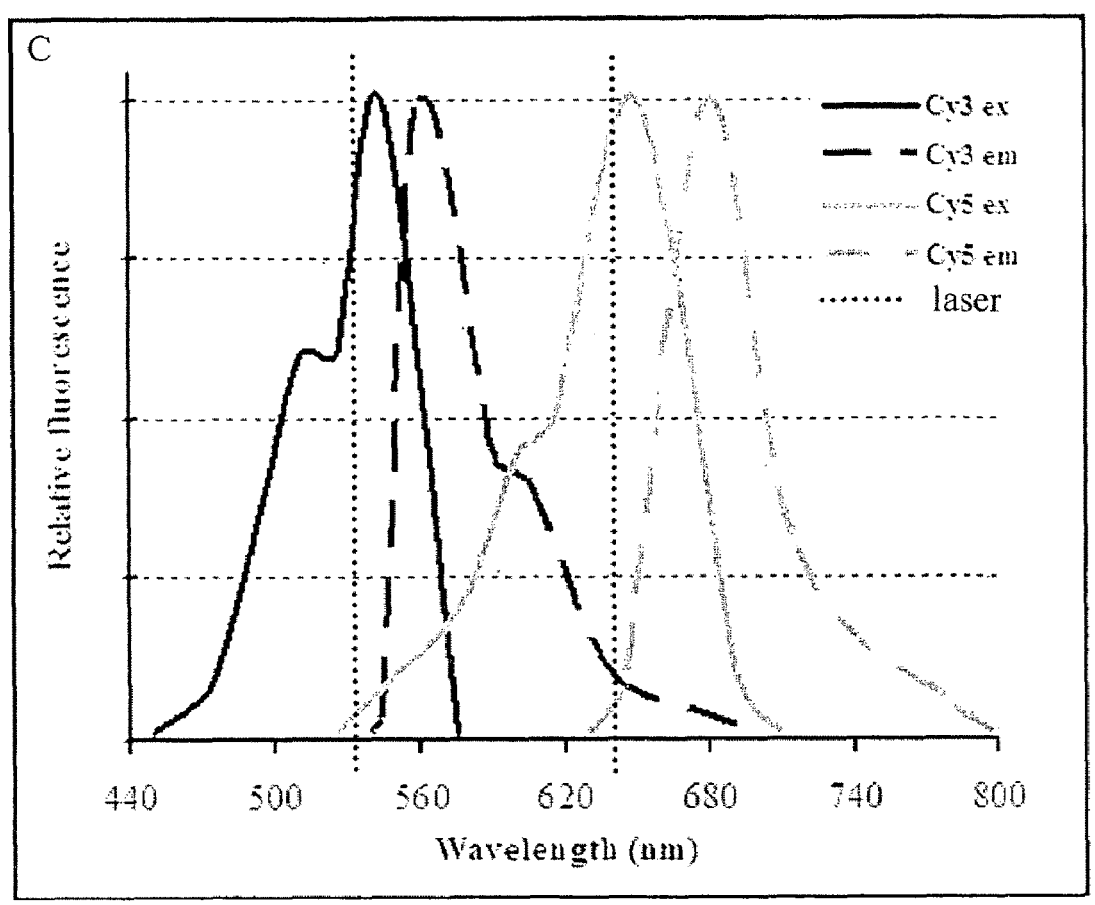
FIG. 3C is a 2-dimensional representation of the fluorescent and wavelength components shown in FIG. 3A, showing the excitation (solid lines) and emission (dashed lines) curves for Cy3 and Cy5.
Figure 3D:
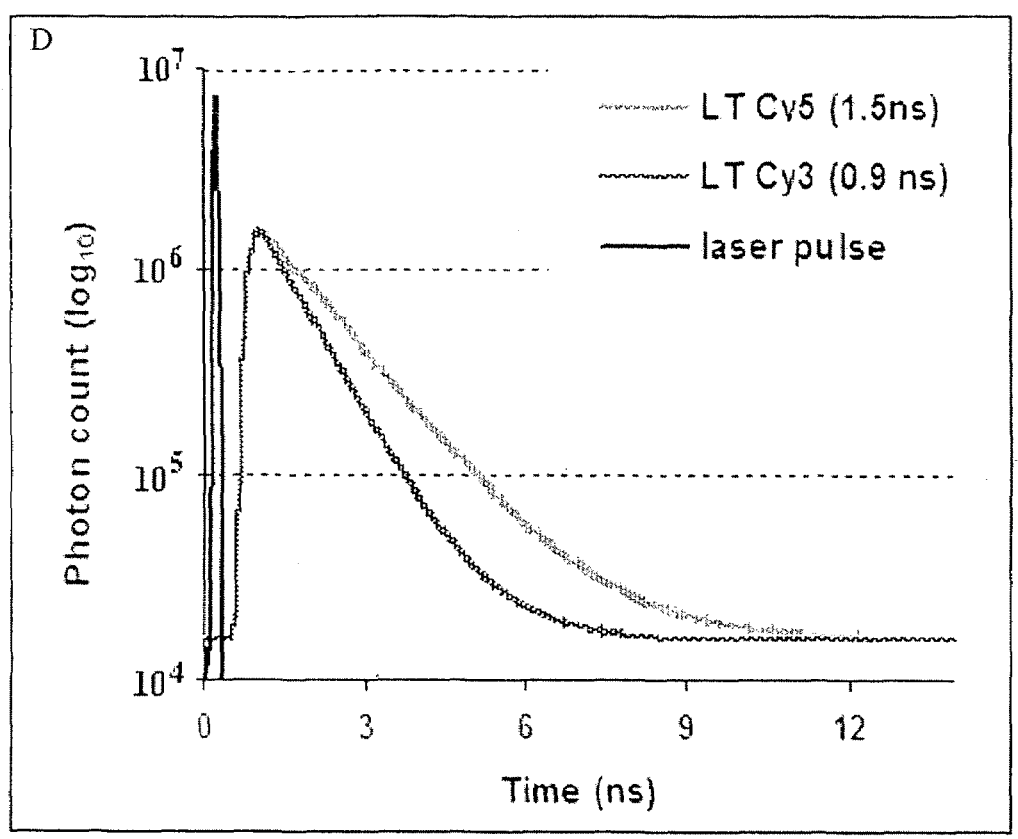
FIG. 3D is a 2-dimensinal representation of the time component and photon count components of FIG. 3B, showing the lifetime emission curevs for Cy3 and Cy5.

FIGS. 3A-3D show this graphically. During excitation with a constant light source (FIG. 3A), as is the case in existing laser scanners used in gel-based proteomics, the excitation curves (FIG. 3C, solid lines) and emission curves (FIG. 3C, dotted lines) have to be sufficiently separated to avoid quenching or overlap between fluorochromes. Due to the constant excitation, the overlap remains the same throughout the measurement (FIG. 3A). Accordingly, a prolonged measurement window results in an amplification of specific and non-specific (background) signals alike. During excitation with a pulsed laser (FIG. 3B), the excitation source becomes temporally (FIG. 3D) as well as spectrally (FIG. 3C) separated from the emission. These spectro-temporal characteristics add another dimension of distinction between different fluorescent species, and provide means for background subtraction at the photon level (see FIG. 2).

Since a constant light source is used for excitation, the spectral overlap between excitation and emission spectra remains (FIG. 3A), making the use of a narrow band pass filter obligatory. In contrast, the spectro-temporal separation provided by the CUTEDGE™ technology separates the excitation and emission spectra in time (FIG. 3B), thus making it possible to use a wider band pass filter with resulting improvements in dynamic range and sensitivity. The use of multiplexing through spectral separation rather than through TRF also decreases the complexity of the life time decay spectra, thus improving the background subtraction capability of the CUTEDGE™ method. The method of spectral separation can also be utilized for simultaneous measurement of multiple probes in cases where the excitation wavelength coincides. Our proof-of-principle measurements indicate that this is the case for the probe pair Cy2 and Cy3, which both can be sufficiently excited by a 490 nm diode laser. Separate detection of emissions can then be facilitated by a use of dichroic filters and dual detectors (see Example 4). Following development of novel fluorochrome sets for TRF-multiplexing with sufficiently large differences in lifetimes such that adequate fitting of both fluorochrome and background components can be achieved, spectral separation methods may be omitted.

Existing image acquisition instrumentation utilizes a PMT for detection of the photons emitted by the excited fluorochrome. While a PMT affords high amplification of the signal (up to $10^6$), the efficiency of the photon counting is generally low (QE~10%). While APD detectors display quantum efficiencies of up to 90% in the visible range, their use in image acquisition instrumentation have previously been hampered by their long down time following each detected photon. New methods for active quenching of APD detectors counteract this problem, and the use of an APD detector may thus offer significant improvements in sensitivity and dynamic range. However in cases where a broad dynamic range is required, the limited maximal count rates of APD type detectors may still be a limiting factor. Accordingly, a range of detectors suitable for the CUTEDGE™ instrument exist, and the dynamic range of detection will be weighted against the sensitivity of detection in the design of individual CUTEDGE™ instruments depending on the desired application.

The extraction of the spectro-temporal characteristics of each fluorochrome used in CUTEDGE™ makes way for new approaches to quantification of the signal. In existing FLIM applications, the amplitude of the signal for each component is generally utilized to quantify the contribution of each component in a pixel. In the CUTEDGE™ application, we will instead utilize the entire area under the curve (AUC) for quantification purposes. The use of the AUC, corresponding to the fitted photon count for each specific component, will contribute to increased sensitivity of detection as well as the dynamic range. In traditional image acquisition, where constant excitation is applied, integration of the AUC does not improve the dynamic range of the measurement notably over amplitude measurements, since all confounding factors are convoluted with the signal of the probe, and thus are amplified along with the specific signal. Given the deconvolution of multi-exponential decay curves used in CUTEDGE™, the AUC specific for the fluorochrome can be calculated. Since the spectro-temporal separation also facilitates the use of a broader band pass emission filter, the signal-to-noise improvements of calculating the resulting volume under the curve (VUC) will be further increased.

Figure 7:
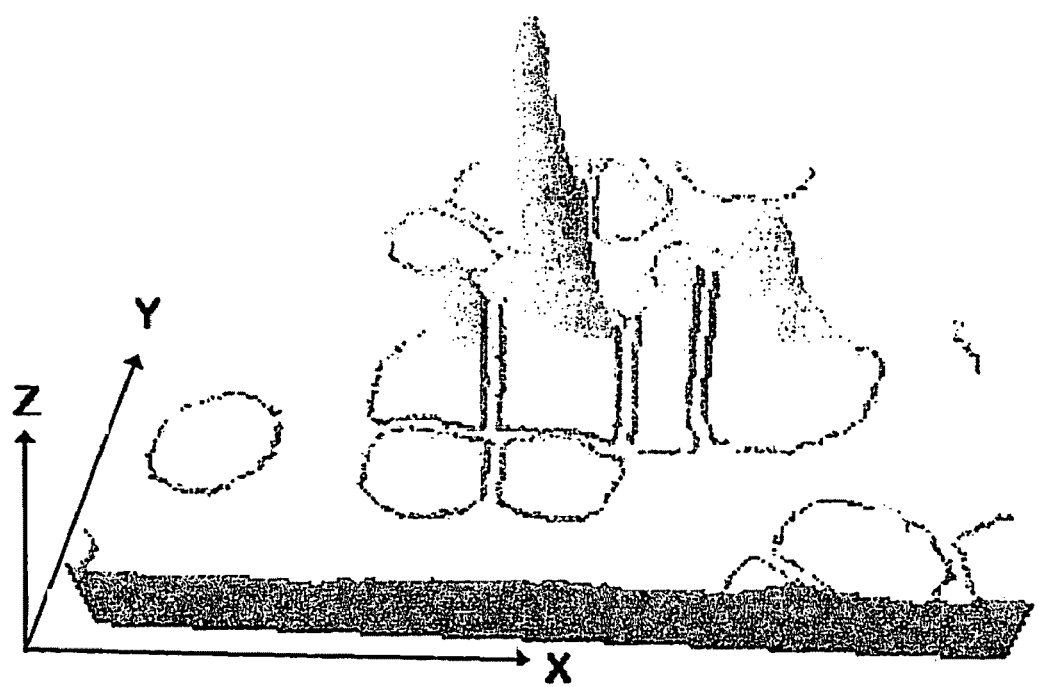
FIG. 7 shows the three dimensions that contribute to the spot volume used for protein quantification.

The need for complex manual assistance and evaluations of the lifetime fitting algorithms available in existing FLIM software puts high demands on the user in terms of in-depth knowledge of the field. In contrast, the CUTEDGE™ concept will provide a high level of automation to allow proteomics researchers without expertise in the field of time resolved fluorescence to perform accurate measurements in a time-efficient manner. Given that the lifetimes of the fluorescent components in 2-DGE remain constant in the light of altered polyacrylamide concentrations and buffers, automated protocols for pixel-wise lifetime fitting and subsequent export of intensity images for the relevant component will be included for the standard fluorochromes used in 2-DGE today. In order to facilitate the use of existing 2-DGE image analysis software, the AUC will thus be represented as a one-dimensional (Z) intensity in the resulting exported image (see FIG. 7). The use of a 32 bit grayscale image file format in replacement of the currently used 16 bit format provides a digital dynamic range of close to 10 orders of magnitude, thus facilitating the multiple order-of-magnitude improvements in dynamic range achieved through the CUTEDGE™ technology. To provide maximal flexibility of the instrument, software for user-guided fitting as well as construction of routines for automated scanning will also be provided to allow easy implementation of protocols for novel fluorochromes or gel matrices.

The time-consuming aspects of 2-DGE often limit its usability in large scale proteomics studies today, and automation is of utmost importance in any proteomics platforms. In addition to the automated lifetime fitting and subsequent calculation of the intensity image for the fluorochrome component described above, automated sequential scanning of multiple protocols as defined by the user will thus be a standard feature in the CUTEDGE™ instrument. Besides time-efficiency, this feature also contributes to minimizing light exposure of the various fluorochromes. Sequential scans facilitate multiplexing, such as exemplified by the minimal DIGE protocol (Example 2). Other applications of sequential scans include detection of total protein with SYPRO™ Ruby following saturation DIGE (Example 5), or four-plexing with an additional CyDye (Example 4).

The CUTEDGE™ instrument will be equipped with variable frequency pulsed lasers (e.g 0.1-40 MHz) to allow fine-tuning of the method used for detection and quantification of the wide range of fluorochromes currently used in 2-DGE. For example, the extremely long life-times of ~350-500 ns reported for Ruthenium complexes (7, 8, 13) would call for a time-delayed, cumulative measurement approach (FIG. 2B, Example 1), while the much shorter life-spans of e.g. the CyDyes (~1 ns (8)) suggest that FLIM with subsequent subtraction of the decay curve derived from the background (FIG. 2A, Example 2) is more appropriate to achieve maximal sensitivity for these fluorochromes. Variable frequency mode will provide a much shorter scan time for the latter.

With respect to the above description then, it is to be realized that the optimum dimensional relationships for the parts of the invention, to include variations in size, materials, shape, form, function and manner of operation, assembly and use, are deemed readily apparent and obvious to one skilled in the art.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

EXAMPLE 1

In this example, proteins are first isolated from rat airway through lysis-lavage (14), an isolation method that instantly solubilizes the airway epithelial proteome in a 2-DGE-compatible urea-based lysis buffer (7M urea, 2M thiourea, 4% w/v CHAPS, 0.5% Triton-X 100, 2% v/v protease inhibitor cocktail). The protein concentration of the samples is determined using the method of Bradford, and separated using 2-DGE. An aliquot of 400 µg protein/sample is diluted to 350 µl with lysis buffer, and IPG buffer for the appropriate pH range is added to a final concentration of 1% v/v. The protein samples are loaded onto the IPG strip (GE Healthcare) through rehydration at room temperature overnight, and isoelectric focusing (IEF) is performed using a Multiphor II Electrophoresis unit and an EPS 3501 XL power supply at 20° C. with the following gradient protocol: 0-50V, 1 min.; 50V, 1 hr; 50-1000V, 3 hr; 1000-3500V, 3 hr; 3500V, 19 hr (total 74.9 kVh). Following IEF, the strips are incubated 2×15 min in equilibration buffer (50 mM tris-HCl pH 8.8, 6 M urea, 30% glycerol, 2% SDS). Reduction and alkylation of sulfhydryls is performed through incorporation of 65 mM DTT in the first incubation, and 10 mM iodoacetamide in the second. The strips are then loaded onto 20 cm×25 cm 10% T SDS-PAGE gels and sealed using 0.5% IsoGel agarose. The second dimension separation is performed in an Ettan Dalt Electrophoresis system (GE Healthcare) at 10° C., 14 mA/gel until the dye front has migrated 18 cm (~18 hrs) in 25 mM Tris, 192 mM glycine, and 0.1% SDS.

The polyacrylamide gel is then removed from the glass cassette, and the proteins are visualized using SYPRO Ruby™ stain according to the manufacturer's protocol (Molecular Probes, Eugene, Oreg.). In brief, the 2-DGE gels are fixed in 7% acetic acid and 10% ethanol for 2×30 min, then incubated in 100% SYPRO™ Ruby staining solution overnight. Subsequently, the 2-DGE gels are destained in 100% methanol for 5 min in order to remove stain particles on the gel surface, then equilibrated in water for 2×15 min.

The SYPRO™ Ruby-stained 2-DGE gel is placed directly on the glass platen of the CUTEDGE™ scanner, and proteins are visualized using a time-delayed multi-exponential lifetime measurement regimen with a pixel size of 20-100 µm. Excitation is performed through a pulsed diode laser of wavelength 490 nm, and a low pulse rate of 0.1-0.5 MHz (2-10 µs cycles) to allow complete decay of the extremely long life-times of the fluorescent Ru complex in SYPRO™ Ruby.

Emission is detected using a PMT detector and a band pass emission filter of 610±50 nm (610 bp 100), alternatively a 600 nm long pass filter, is applied. The data is exported to a multi-exponential fluorescence decay fitting software module capable of fitting up to four different decay algorithms simultaneously. Based on the extremely long fluorescent lifetime of the rutheniumII-tris(bathophenanthrolinedisulfonate) (RuTBS) molecule used in the SYPRO™ Ruby protein stain, a time-delayed measurement approach is utilized to exclude background fluorescence (FIG. 2B). The area under the curve (AUC) of the decay curve for the RuTBS molecule over the time interval 10-500 ns is calculated, and defined as the pixel intensity for the given X, Y coordinate of the scanner position (see FIG. 7).

The time delayed measurements facilitate maintained selectivity with a broader band pass emission filter as compared to that normally used for the SYPRO™ Ruby stain (610 bp 30), since the majority of the auto-fluorescence from the matrix and biomolecules occurs during the first 5 ns. The broader band pass filter allows detection of the bulk of the broad emission peak for RuTBS, with increased sensitivity as a result. Following completion of the scan, the resulting AUC values for each respective X, Y coordinate are merged into a 32 bit grayscale tiff file which can be analyzed by a 2-DGE analysis software of choice.

EXAMPLE 2

Macrophages isolated by bronchoalveolar lavage from smoking and never-smoking human subjects are solubilised using 2-DGE lysis buffer (see Example 1). An internal standard is created through pooling of equal amounts of protein from all the subjects included in the study, and labelled with NHS ester-conjugated Cy2 (minimal DIGE reagent) according to the manufacturer's recommendations (GE Healthcare, Uppsala, Sweden). The protein samples from smoker and never-smoker subjects are randomized into two groups, which are labeled with Cy3 and Cy5 minimal DIGE reagents respectively. The Cy2 labeled internal standard is co-separated with one Cy3 and one Cy5 labeled sample on a 2-DGE gel according to the protocol described in Example 1. The three different protein labels are visualized in an automated sequence of three different scanning protocols using a combination of spectral and time-resolved fluorescence as follows:

A) The Cy2 fluorochrome (internal standard) is excited through a pulsed diode laser of wavelength 490 nm, and a pulse rate of 40 MHz (25 ns cycles). Emission is detected using an APD detector with a response rate of 50 ps, and a band pass emission filter of 520±20 nm (520 bp40) is applied.

B) The Cy3 fluorochrome (sample) is excited through a pulsed diode laser of wavelength 532 nm, and a pulse rate of 40 MHz (25 ns cycles). Emission is detected using an APD detector with a response rate of 50 ps, and a band pass emission filter of 580±10 nm (580 bp20) is applied.

C) The Cy5 fluorochrome (sample) is excited through a pulsed diode laser of wavelength 640 nm, and a pulse rate of 40 MHz (25 ns cycles). Emission is detected using an APD detector with a response rate of 50 ps, and a band pass emission filter of 670±10 nm (670 bp20) is applied.

Figure 6:
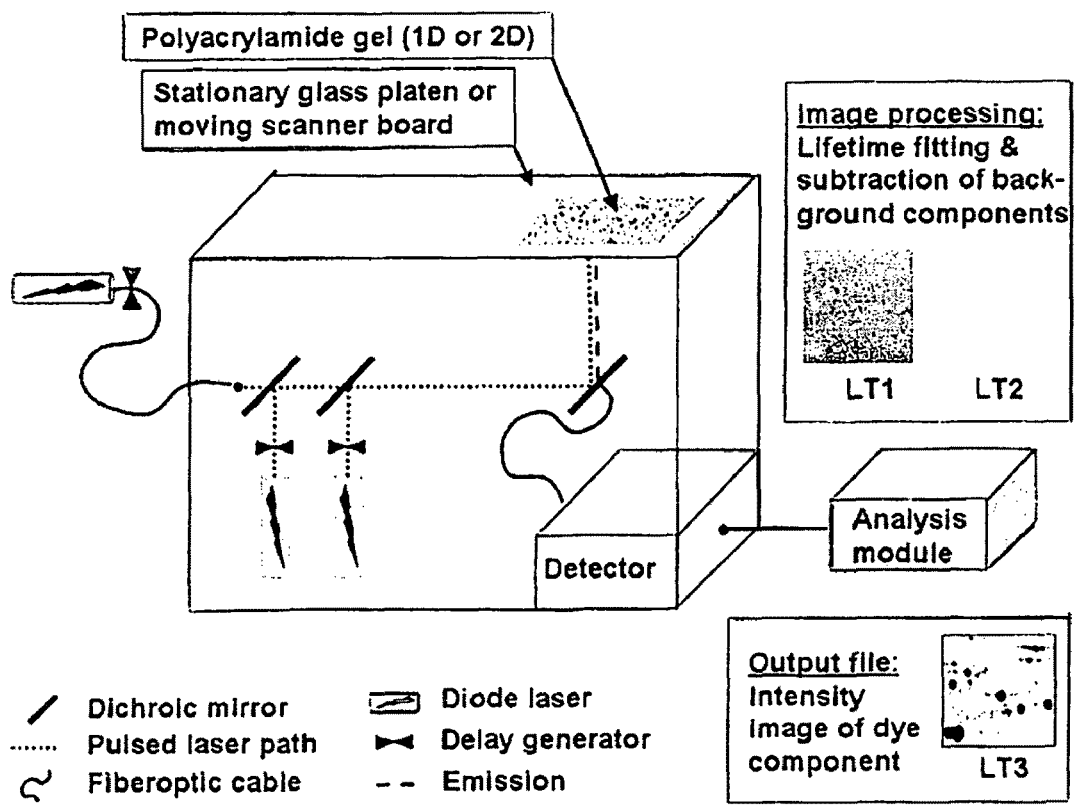
FIG. 6 is a schematic over a potential CUTEDGE™ instumental design.

The data from each of the scanning procedures are exported to a multiexponential fluorescence decay fitting software module capable of fitting multiple decay algorithms simultaneously. Due to the relatively short decay times of the CyDyes (0.9-1.5 ns) the AUC under the entire decay curve corresponding to the respective CyDye is calculated for each pixel (FIG. 2A). The multidimensional fitting of the decay curves facilitates subtraction of the background emission on a photon level on each of the specific wavelengths, which is provided as an automated feature in the software module (FIG. 6). The resulting AUC values for each respective X, Y coordinate are merged into three distinct superimposable 32 bit grayscale image files suitable for analysis with a 2-DGE analysis software with DIGE capability

EXAMPLE 3

As an additional step to the protocol described in Example 2, SYPRO™ Ruby staining is performed to facilitate quantification of the total protein content in the DIGE gel. In existing technology, it is not possible to utilize the DIGE and SYPRO™ Ruby fluorochromes in the same 2-DGE gels due to spectral overlap, particularly in terms of the emission curves of SYPRO™ Ruby, Cy3 and Cy5. The embodiments of this invention utilize the temporal dimension to facilitate merging of these to standard protocols (as exemplified in FIG. 3). Following completion of the procedures outlined in Example 2, post-staining with SYPRO™ Ruby staining to quantify total protein content is performed according to steps B and C outlined in Example 1.

EXAMPLE 4

The current invention facilitates four-plexed DIGE analysis though use of an additional CyDye, such as Cy5.5 or Cy7. A fourth sample is labeled with the additional CyDye-NHS-ester conjugate, and co-separated with the Cy2-labelled internal standard and Cy3- and Cy5-labelled samples as described in Example 2. In the case of incorporation of the Cy7 fluorochrome, an additional visualization step is added to Example 2 through excitation with a pulsed diode laser of wavelength 735 nm, a pulse rate of 40 MHz (25 ns cycles), and an emission filter of 780±30 nm (780 bp60). In the case of corporation of Cy5.5, an alternative method using dual detectors can be applied to greatly reduce the total scan time: Proof-of-principle measurements have shown that the overlap in excitation wavelengths of Cy2 and Cy3 is sufficient to allow excitation of both fluorochromes with a single diode laser of 490 nm.

Through applying a dichroic filter to split the emitted light beam based on wavelength, the emission from both fluorochromes can be detected simultaneously by use of dual detectors. Since the spectral overlap of Cy5 and Cy5.5 resembles that of the dye pair Cy2/Cy3, a single scan/dual detection method can be applied also for this dye pair using a 640 nm pulsed laser and appropriate dichroic filter in combination with emission filters 670 BP20 and 710BP40 nm respectively. The data from each detector/scan protocol are exported to a multi-exponential fluorescence decay fitting software module. The AUC under the fitted decay curve corresponding to the respective CyDye is calculated for each pixel. The multidimensional fitting of the decay curves facilitates subtraction of the background emission on a photon level on each of the specific wavelengths (FIG. 6). The resulting AUC values for each respective X, Y coordinate are merged into four distinct superimposable 32 bit grayscale tiff files suitable for analysis with a 2-DGE analysis software with DIGE capability.

EXAMPLE 5

This example involves an alteration of the recently published method for determination of the redox status of protein thiols, where Spiess et al. (15) utilized Saturation DIGE multiplexing to detect oxidation or adduct formation of cysteines following exposure to oxidants. In brief, airway epithelial proteins are isolated through lysis lavage using non-thiourea lysis buffer (14), and incubated with an excess of maleimide-conjugated Cy3 label (250 nM Cy3/mg protein; >10-fold excess) for labeling of reduced thiols. Incubations of 16 hours are performed to assure complete hydrolysis of free (excess) Cy3 label. Subsequently, tributylphosphine is added to a final concentration of 24 mM to reduce disulfide bonds. A second saturation labeling reaction using Cy5 maleimide is performed in order to label the cysteines of the reduced disulfide bonds. The differentially labeled protein samples are separated by 2-DGE as described in Example 1. In the original method, Cy3 and Cy5 levels were quantified using a Typhoon 8600 fluorescent scanner (Molecular Dynamics, Sunnyvale, Calif., part of GE Healthcare) which utilizes a constant light source for excitation. Total protein content determined through silver staining (see FIG. 1) was used for normalization.

By means of the current invention, the sensitivity, specificity and dynamic range of method described above can be improved by a combination of the protocols described in Example 2 and Example 3. In brief, this include visualization of the CyDyes using the CUTEDGE™ technology as described in Example 2, followed by quantification of total protein content using the CUTEDGE™ SYPRO™ Ruby protocol described in Example 3.

EXAMPLE 6

Proteins from broncheoalveolar lavage (BAL) fluid from asthmatic patients as well as healthy control subjects are analyzed for IL-13 content though immunoblotting. In brief, BAL fluid proteins are concentrated using a BioMax centrifugal filter according to the manufacturer's instructions (Millipore, Bedfont, Oreg.) and separated with 2-DGE as described in Example 1. Following electrophoresis, the proteins are blotted to Sequiblot™ polyvinyldiflouride (PVDF) membranes (0.2 µm pore size) using the ISO-DALT system at 10° C., 250 mA for 19 hours in 25 mM Tris, 192 mM glycine, 10% (v/v) methanol. Subsequently, blocking of the membrane with milk protein is performed, and PVDF membranes are incubated with a monoclonal anti-IL-13 primary antibody. The primary antibody is detected using a Cy5-conjugated anti-mouse secondary antibody.

The Cy5 label is visualized through excitation with a 640 nm pulsed diode laser (40 MHz), and fluorescence is quantified through an APD detector with a response rate of 50 ps and a 670 bp20 emission filter. The data is exported to a multiexponential fluorescence decay fitting software module capable of fitting multiple decay algorithms simultaneously. The AUC under the entire decay curve is calculated for each pixel. The multidimensional fitting of the decay curves facilitates subtraction of the background emission on a photon level on each of the specific wavelengths. The resulting AUC values for each respective X, Y coordinate are merged into a 32 bit grayscale tiff file suitable for analysis with a 2-DGE analysis software.

While the invention has been described with reference to specific embodiments, it will be appreciated that numerous variations, modifications, and embodiments are possible, and accordingly, all such variations, modifications, and embodiments are to be regarded as being within the spirit and scope of the invention.

References

1. Wheelock A M, Goto S. 2006. Effects of post-electrophoretic analysis on variance in gel-based proteomics. *Expert Rev. Proteomics.* 3: 129-142
2. Wheelock A M, Buckpitt A R. 2005. Software-induced variance in two-dimensional gel electrophoresis image analysis. *Electrophoresis* 26: 4508-4520
3. Wheelock A M, Wheelock C E. 2008. Bioinformatics in gel-based proteomics. In *Plant Proteomics: Technologies, Strategies and Applications*, ed. R Rakwal, G Agrawal, pp. 107-125. Hoboken, N.J., USA: John Wiley & Sons Inc.
4. Silva E, O'Gorman M, Becker S, Eklund A, Grunewald J, Wheelock A M. In the eye of the beholder: Does the Master see the SameSpots as the novice? *Journal of Proteome Research*: Under revision
5. Suhling K, French P M, Phillips D. 2005. Time-resolved fluorescence microscopy. *Photochem Photobiol Sci* 4: 13-22
6. Wallrabe H, Periasamy A. 2005. Imaging protein molecules using FRET and FLIM microscopy. *Curr Opin Biotechnol* 16: 19-27
7. Handl H L, Gillies R J. 2005. Lanthanide-based luminescent assays for ligand-receptor interactions. *Life Sci.* 77: 361-371
8. Clapp A R, Medintz I L, Fisher B R, Anderson G P, Mattoussi H. 2005. Can luminescent quantum dots be efficient energy acceptors with organic dye donors? *J. Am. Chem Soc.* 127: 1242-1250
9. Alban A, David S O, Bjorkesten L, Andersson C, Sloge E, Lewis S, Currie I. 2003. A novel experimental design for comparative two-dimensional gel analysis: two-dimensional difference gel electrophoresis incorporating a pooled internal standard. *Proteomics.* 3: 36-44
10. Wheelock A M, Morin D, Bartosiewicz M, Buckpitt A R. 2006. Use of a fluorescent internal protein standard to achieve quantitative two-dimensional gel electrophoresis. *Proteomics* 6: 1385-1398
11. Lassiter S J, Stryjewski W, Legendre B L, Jr., Erdmann R, Wahl M, Wurm J, Peterson R, Middendorf L, Soper S A. 2000. Time-resolved fluorescence imaging of slab gels for lifetime base-calling in DNA sequencing applications. *Anal Chem* 72: 5373-5382
12. Stryjewski W, Soper S A, Lassiter S J, Davis L. 2002. Multiplexed analysis using time-resolved near-IR fluorescence for the detection of genomics material. *Proceedings of SPIE* 4626: 201-209
13. Bartolome A, Bardliving C, Rao G, Tolosa L. 2005. Fatty acid sensor for low-cost lifetime-assisted ratiometric sensing using a fluorescent fatty acid binding protein. *Anal. Biochem.* 345: 133-139
14. Wheelock A M, Zhang L, Tran M U, Morin D, Penn S, Buckpitt A R, Plopper C G. 2004. Isolation of rodent airway epithelial cell proteins facilitates in vivo proteomics studies of lung toxicity. *Am. J. Physiol Lung Cell Mol. Physiol* 286: L399-L410
15. Spiess P C, Morin D, Jewell W T, Buckpitt A R. 2008. Measurement of protein sulfhydryls in response to cellular oxidative stress using gel electrophoresis and multiplexed fluorescent imaging analysis. *Chem Res Toxicol* 21: 1074-1085

The invention claimed is:

1. An improved method of image acquisition of one-dimensional or two-dimensional gel electrophoresis, comprising excitation of a fluorochrome bound to a protein with a pulsed laser scanner to provide fluorescent lifetime imaging measurements for detection and quantification of proteins on a pixel-by-pixel level, and utilizing multiexponential fitting of the fluorescence decay curve to separate fluorescence originating from the fluorochrome-labeled protein species from fluorescence originating from other sources, the sources selected from the group consisting of a gel matrix, solutions or particles present in the gel, a blotting membrane, and scattering effects, for subsequent background subtraction.

2. The method of claim 1, wherein the pulsed laser scanner is a diode laser internally housed within a sealed scanner enclosure.

3. The method of claim 1, wherein the pulsed laser scanner is externally attached through fiberoptic cable outlets to provide optimal flexibility in terms of the excitation wavelengths to be used.

4. The method of claim 1, wherein the method is performed on up-graded existing instrumentation.

5. The method of claim 1, wherein the method is performed on a fully enclosed scanner system.

6. The method of claim 1, wherein the fluorescence from other sources originates from the blotting membrane.

7. The method of claim 1, further comprising sequential use of multiple laser wavelengths for excitation to facilitate a combination of time-resolved fluorescence with spectral separation of fluorochromes, using multiplexing through spectral separation to decrease the complexity of the life time decay spectra.

8. The method of claim 7, wherein there are with dual fluorescent lifetime imaging measurements.

9. The method of claim 1, further comprising integrating an intensity fluorescent decay curve specific for the fluorochrome to calculate the area under the curve.

10. The method of claim 1, further comprising incorporating automation and user-friendly features.

11. The method of claim 10, wherein the automation and user-friendly features include at least one of graphical and quantitative calculations of acquired one- or two-dimensional gel electrophoresis, automated protocols for fluorescent lifetime imaging analysis, subtraction of the background components, and export of intensity images for the fluorochrome component(s) for the standard fluorochromes used in two-dimensional gel electrophoresis.

12. The method of claim 1, further comprising maximizing automation, facilitation of programming of sequential scanning of multiple different protocols as defined by the user, including sequential scanning of multiple fluorochromes used for multiplexing.

13. The method of claim 1, further comprising use of fluorescent probes used in gel-based proteomics, and variable frequency pulsed laser diodes for optimization of scan times.

14. The method of claim 1, further comprising a blotting step, wherein the detection and quantification of proteins comprises quantification of fluorescence after the blotting step.

* * * * *